United States Patent [19]

Egalon et al.

[11] Patent Number: 5,249,251
[45] Date of Patent: Sep. 28, 1993

[54] OPTICAL FIBER SENSOR HAVING AN ACTIVE CORE

[75] Inventors: Claudio O. Egalon; Robert S. Rogowski, both of Hampton, Va.

[73] Assignee: The United States of America as represented by the Administrator of the National Aeronautics and Space Administration, Washington, D.C.

[21] Appl. No.: 855,363

[22] Filed: Mar. 18, 1992

Related U.S. Application Data

[63] Continuation-in-part of Ser. No. 761,198, Sep. 16, 1991.

[51] Int. Cl.[5] .......................... G02B 6/16; G02B 6/22
[52] U.S. Cl. ................... 385/123; 385/126; 385/127; 385/128; 385/142; 372/6
[58] Field of Search ............... 385/12, 13, 123, 126, 385/127, 128, 142; 250/227.14, 458.1, 459.1, 461.1, 461.2; 372/6

[56] References Cited

U.S. PATENT DOCUMENTS

| | | | |
|---|---|---|---|
| 4,560,248 | 12/1985 | Cramp et al. | 385/12 |
| 4,790,619 | 12/1988 | Lines et al. | 385/12 |
| 4,824,206 | 4/1989 | Klainer et al. | 385/12 |
| 4,834,496 | 5/1989 | Blyler, Jr. et al. | 385/12 |
| 4,852,967 | 8/1989 | Cook et al. | 385/12 |
| 4,880,752 | 11/1989 | Keck et al. | 385/12 |

OTHER PUBLICATIONS

A. Tanaka et al., "New plastic optical fiber using polycarbonate core and fluorecence-doped fiber for high temperature use", *Fiber and Integrated Optics*, vol. 7, (1987), pp. 139-158.

H. Sawada et al., "Plastic optical fiber doped with organic fluorescent material", *Fiber Optic Systems for Mobile Platgorms II, SPIE*, vol. 989, 1988, pp. 133-139.

Fluorescent Plastic Optical Fiber, Fujitsu Limited Product Bulletin (Published as of 1991), 4 pages.

K. Kurosawa et al., "Diagnostic technique for electrical power equipment using fluorescent fiber", (Article published as of 1991), 7 pages.

Egalon, Claudio O., "Injection efficiency of bound modes", NASA Contractor Report 4333, Nov. 1990.

Marcuse, D., "Launching light into fiber cores from sources located in the cladding", J. of Lightwave Tech., vol. 6, No. 8, Aug. 1988, pp. 1273-1279.

Lewis, N. E. et al., Fiber Optic Systems for Mobile Platforms II, SPIE vol. 989, "Plastic optic fiber doped with organic fluorescent materials", Sep. 1988, pp. 133-139.

Tanaka, A. et al., "New plastic optical fiber using polycarbonate core and fluorescence-doped fiber for high temperature use", Fiber and Integrated Optics, vol. 7, Aug. 1987, pp. 139-158.

Lieberman, R. A. et al., "Intrinsic fiber optic chemical sensor based on two-stage fluorescence coupling", SPIE vol. 990, Chemical, Biochemical, and Environmental Applications of Fibers, 1988, pp. 104-110.

*Primary Examiner*—Frank Gonzalez
*Attorney, Agent, or Firm*—Kevin B. Osborne

[57] ABSTRACT

An optical fiber is provided comprising an active fiber core which produces waves of light upon excitation. A factor ka is identified and increased until a desired improvement in power efficiency is obtained. The variable "a" is the radius of the active fiber core and "k" is defined as $2\pi\lambda$, wherein $\lambda$ is the wavelength of the light produced by the active fiber core. In one embodiment, the factor ka is increased until the power efficiency stabilizes. In addition to a bare fiber core embodiment, a two-stage fluorescent fiber is provided wherein an active cladding surrounds a portion of the active fiber core having an improved ka factor. The power efficiency of the embodiment is further improved by increasing a difference between the respective indices of refraction of the active cladding and the active fiber core.

26 Claims, 4 Drawing Sheets

OPTICAL FIBER SENSOR HAVING AN ACTIVE CORE

ORIGIN OF THE INVENTION

The invention described herein was jointly made in the performance of work under a NASA contract and an employee of the United States Government. In accordance with 35 U.S.C. 202, the contractor elected not to retain title.

CROSS-REFERENCE

This application is a continuation-in-part application of pending patent application Ser. No. 07/761,198, filed Sep. 16, 1991, now allowed.

BACKGROUND OF THE INVENTION

1. Technical Field of the Invention

The present invention relates generally to an optical fiber fluorosensor and more particularly to an improved fluorosensor having an active core for determining the concentration of a chemical species.

2. Related Art

Active optical fiber sensors have been developed for determining the concentration of a particular analyte or chemical species. The sensors basically fall into three groups—sensors having an active fluorescent cladding, sensors having an active fluorescent core, and sensors having both an active cladding and core. It is desirable to maximize the power efficiency of such a fiber sensor, as discussed in NASA Contractor Report 4333, "Injection Efficiency of Bound Modes", by Claudio Oliveira Egalon, Contract NAS1-18347, Nov. 1990. This report observes the power efficiency $P_{eff}$ of active cladding optical fibers, wherein a is the core radius and $k = 2\pi/\lambda$, wherein $\lambda$ is the wavelength of the light emitted by the cladding sources. See pp. 80–82. As ka was increased by varying the core radius a, a decrease in power efficiency was observed in a bulk distribution of cladding sources and an increase was observed in a thin film distribution. See p. 110 and FIGS. IV-10 and IV-11. Similar relationships were found when $\lambda$ was varied. See p. 101 and FIG. IV-6(b). There was no consideration of the effect of varying ka of an active core optical fiber.

OBJECTS OF THE INVENTION

It is accordingly an object of the present invention to improve the power efficiency of an optical fiber having an active fiber core.

It is another object of the present invention to optimize the power efficiency of an optical fiber having an active fiber core.

It is a further object of the present invention to accomplish the foregoing objects in a simple, straightforward manner.

Other objects and advantages of the present invention are apparent from the specification and drawings which follow.

SUMMARY OF THE INVENTION

The foregoing and additional objects are obtained according to the present invention. An optical fiber is provided comprising an active fiber core which produces waves of light upon excitation. A factor ka is identified and increased until a desired improvement in power efficiency is obtained. The variable "a" is the radius of the active fiber core and "k" is defined as $2\pi/\lambda$, wherein $\lambda$ is the wavelength of the light produced by the active fiber core. In one embodiment, the factor ka is increased until the power efficiency stabilizes. In addition to a bare fiber core embodiment, a two-stage fluorescent fiber is provided wherein an active cladding surrounds a portion of the active fiber core having an increased ka factor. The power efficiency of the embodiment is further improved by increasing a difference between the respective indices of refraction of the active cladding and the active fiber core.

DETAILED DESCRIPTION OF THE INVENTION

Figure 1:
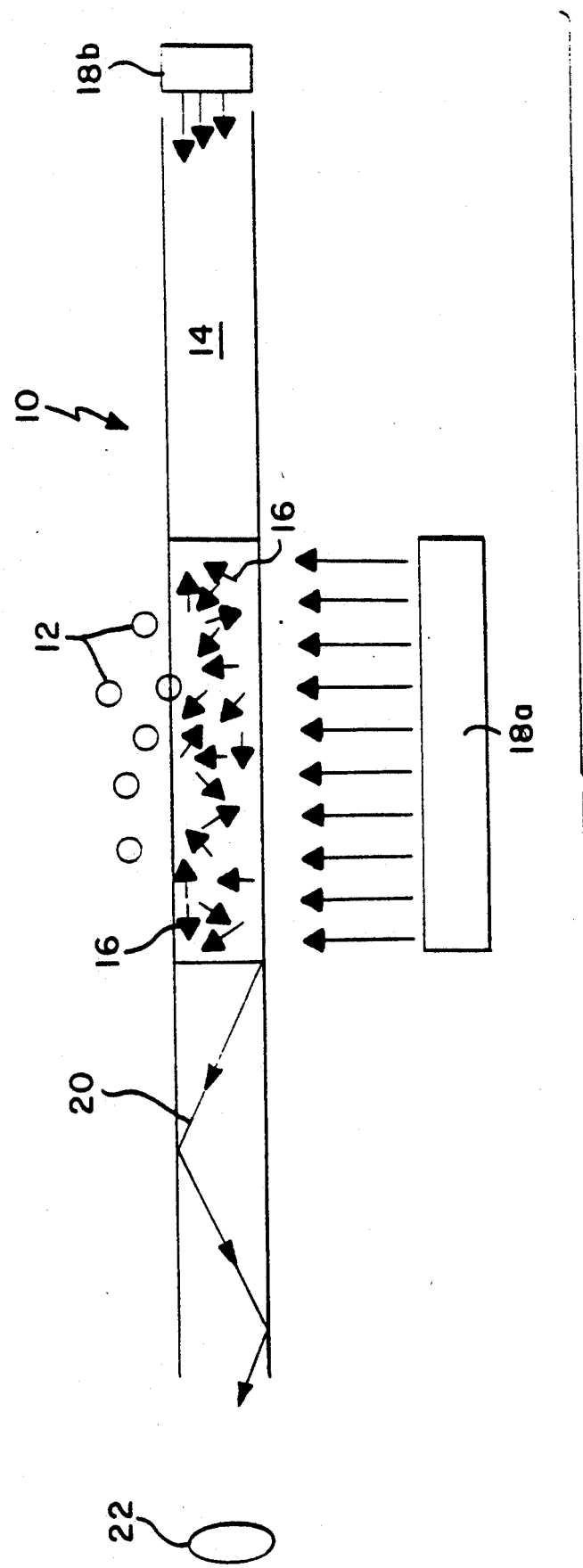
FIG. 1 is an exposed side view of an optical fiber fluorosensor having a bare active fiber core according to the present invention.

An active core index step index profile optical fiber sensor 10, also known as a distributed optical sensor, is shown generally in FIG. 1. The sensor provides information concerning the concentration of a chemical species or analyte 12 via interaction of the analyte with core sources or reagents. A portion of an active fiber core 14 of the sensor is implanted with fluorescent or chemiluminescent substances 16 which can be modeled as dipole sources that are uniformly distributed in the core and have random phase and orientation. The substances are excited by either an outside light source 18a or 18b in the case of fluorescent substances or a direct chemiluminescent reaction with the analyte 12 in the case of chemiluminescent reaction with the analyte 12. The outside source can be located such that the light impinges on the core in a direction perpendicular to the core axis via source 18a or along the core axis from a source 18b located at an end opposite to an intensity detector 22. The sources excite bound modes 20 in core 14 and the resulting light waves are guided to the detector 22. The intensity of the detected light is indicative of the concentration of the chemical species, as known.

The first specific embodiment of the present invention shown in FIG. 1 utilizes a bare active core fiber wherein the core is permeable to the analyte. In this case, the analyte permeates through the core and reacts with the implanted light producing substances. The reaction either produces chemiluminescence or would decrease the fluoroluminescence produced by an outside light source via fluorescent quenching. As discussed, the intensity measured with detector 22 is indicative of analyte concentration.

Figure 2:
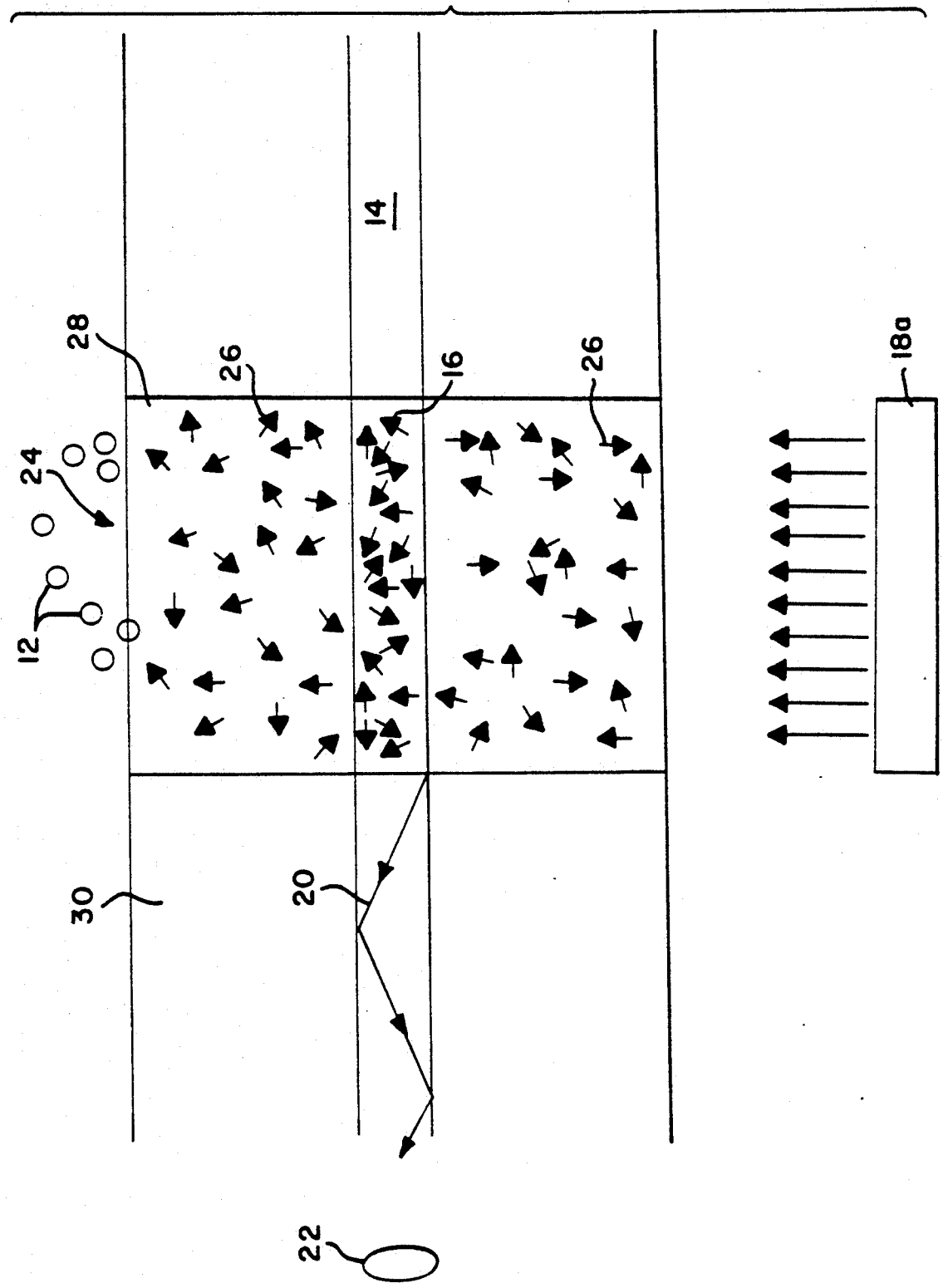
FIG. 2 is an exposed side view of an optical fiber fluorosensor having active and inactive claddings surrounding an active fiber core.

A second specific embodiment of a fiber sensor 24 utilizes a permeable active cladding 30, which surrounds the active fiber core 14, as shown in FIG. 2. The cladding has fluorescent or chemiluminescent substances 26 implanted therein which react directly with the analyte or via light excitation by an outside source 18a as discussed above with reference to substances 16 implanted in a bare active fiber core. The resulting light produced by substance 26 then acts as an "external" light source which excites the fluorescent substances 16 located in the active fiber core 14. As before, the intensity of the light resulting from this so-called two-stage fluorescence is detected as an indication of analyte concentration. The cladding 30 can comprise an active cladding portion 28 containing sources 26 and an inactive guide cladding portion which guides the produced light to the sensor 22. Also, the active cladding may surround the entire fiber core and guide the produced light, dispensing with the need for an inactive guide cladding. In the embodiment of this paragraph, the active fiber core need not be permeable by the analyte.

The power efficiency $P_{eff}$ of an active core optical fiber at one end of the fiber is defined as the ratio of the power that is excited in the active fiber core as bound modes, $P_{core}$, to the total power radiated by the sources, i.e., by $$P_{eff} = \frac{P_{core}}{P_{rad} + 2P_{core}}, \quad (1)$$

wherein $P_{rad}$ is the power due to the radiation modes and the multiplicative factor of 2 was introduced to account for both forward and backward propagating modes.

Figure 3:
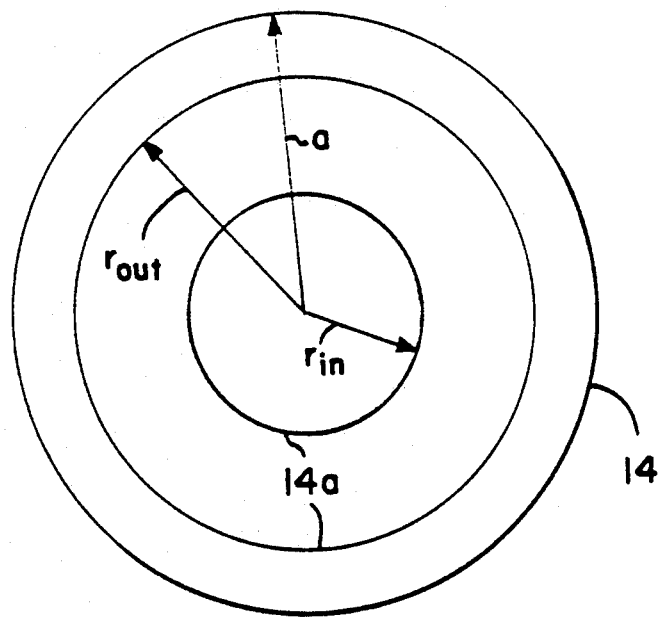
FIG. 3 is an exposed front view of an active fiber core showing the source distribution.

The core sources can be treated an many infinitesimal electric currents with random phase and orientation which excite radiation fields and bound modes. The radiation fields radiate away from the fiber, whereas the bound modes are trapped inside the core and propagate in both forward and backward directions. The expressions for $P_{rad}$ and $P_{core}$ follow:

$$P_{rad} = \sqrt{\frac{\mu_o}{\epsilon_o}} \, \frac{n_{clad}k^2SL}{4} (r_{out}^2 - r_{in}^2) \quad (2)$$

$$P_{core} = \sum_{\nu,\mu} \frac{1}{16P_{\nu,\mu}} \int_{V_{source}} S|e_{\nu,\mu}(r)|^2 dV \quad (3)$$

where L is the length of the fiber with fluorescent sources, k is the circular wavenumber of the fluorescent light, $n_{clad}$ is the index of refraction of the cladding, S is the source strength, $P_{\mu,\nu}$ is a normalization constant, $e_{\mu,\nu}$ is the modal electric field and $r_{out}$ and $r_{in}$ are the outer and inner radii of the core source distribution 14a, as shown in FIG. 3.

For the weakly guiding case the integral in Equation (3) has the same functional form for every mode. However, for the exact case, we are left with computing Equation (3) for each mode separately; transverse electric ($TE_{o,\mu}$), transverse magnetic ($TM_{o,\mu}$) and hybrid modes ($EH_{\nu,\mu}$ and $HE_{\nu,\mu}$). The results for an uniform cylindrical distribution of sources between the radii $r_{in}$ and $r_{out}$ are given below.

For $TE_{o,\mu}$ modes:

$$\int_{V_{source}} |e_{\nu,\mu}(r)|^2 dV = \quad (4a)$$

$$\frac{\pi L a^2}{J_1^2(U_{0,\mu})} (R_{out}^2 |J_1(U_{0,\mu}R_{out})| - R_{in}^2 |J_1(U_{0,\mu}R_{in})|)$$

For $TM_{o,\mu}$ modes:

$$\int_{V_{source}} |e_{\nu,\mu}(r)|^2 dV = \quad (4b)$$

$$\frac{\pi L}{J_1^2(U_{0,\mu})} (a^2(R_{out}^2 |J_1(U_{0,\mu}R_{out})| - R_{in}^2 |J_1(U_{0,\mu}R_{in})|) +$$

$$- \frac{U_{0,\mu}^2}{\beta_{0,\mu}^2} (R_{out}^2 |J_0(U_{0,\mu}R_{out})| - R_{in}^2 |J_0(U_{0,\mu}R_{in})|))$$

For $EH_{\nu,\mu}$ and $HE_{\nu,\mu}$ modes ($\nu > 0$):

$$\int_{V_{source}} |e_{\nu,\mu}(r)|^2 dV = \quad (4c)$$

$$\frac{\pi L}{J_\nu^2(U_{\nu,\mu})} (a^2(R_{out}^2(a_1^2|J_{\nu-1}(U_{\nu,\mu}R_{out})| + a_2^2|J_{\nu+1}(U_{\nu,\mu}R_{out})|) -$$

$$R_{in}^2(a_1^2|J_{\nu-1}(U_{\nu,\mu}R_{in})| + a_2^2|J_{\nu+}(U_{\nu,\mu}R_{in})|)) +$$

$$\frac{U_{\nu,\mu}^2}{2\beta_{\nu,\mu}^2} (R_{out}^2 |J_\nu(U_{\nu,\mu}R_{out})| - R_{in}^2 |J_\nu(U_{\nu,\mu}R_{in})|))$$

where a is the radius of the fiber core, $R_{in} = r_{in}/a$ and $R_{out} = r_{out}/a$ are the normalized inner and outer radii of the source distribution $\beta_{\nu,\mu}$ is the propagation constant, $n_{core}$ is the index of refraction of the core, $a_1$ through $a_6$ are given by Table 12-3(b) of Synder et al in *Optical Waveguide Theory*, Chapman and Hall, New York, 1983, and $J_\nu$ is the Bessel function. Also, we have $$|J_l(A)| = \begin{vmatrix} J_l(A) & J_{l+1}(A) \\ J_{l-1}(A) & J_l(A) \end{vmatrix} \quad (5a)$$

$$U_{\nu,\mu} = a\sqrt{k^2 n_{core}^2 - \beta_{\nu,\mu}^2}, \quad (5b)$$

$$W_{\nu,\mu} = a\sqrt{\beta_{\nu,\mu}^2 - k^2 n_{clad}^2} \text{ and} \quad (5c)$$

$$V = a\sqrt{k^2 n_{core}^2 - k^2 n_{clad}^2} = \sqrt{U_{\nu,\mu}^2 + W_{\nu,\mu}^2}. \quad (5d)$$

Where $U_{\nu,\mu}$ and $W_{\nu,\mu}$ can be found with the help of the eigenvalue equations. Equations (4a–c) were determined using the field relations of Synder et al, Table 12-3, supra.

Notice that the power efficiency can be rewritten in terms of the ratio $P_{ratio} = P_{core}/P_{rad}$ whose expression is much simpler than $P_{eff}$. For this reason, $P_{ratio}$ is displayed for the TE, TM and hybrid modes of the exact solution of the cylindrical fiber with an uniform distribution of sources in its core, i.e., for $R_{in} = 0$ and $R_{out} = 1.0$, by the following:

$$P_{ratio}|TE = \frac{1}{2n_{clad}ka^2V^2} \sum_\mu \frac{W_{0,\mu}^2 |J_1(U_{0,\mu})|}{\beta_{0,\mu} J_0(U_{0,\mu}) J_2(U_{0,\mu})} \quad (6a)$$

$$P_{ratio}|TM = \sum_\mu \frac{\beta_{0,\mu}\left(|J_1(U_{0,\mu})| + \frac{U_{0,\mu}^2}{\beta_{0,\mu}^2 a^2}|J_0(U_{0,\mu})|\right)}{2n_{clad}k^3 a^2 n_{core}^2 J_1^2(U_{0,\mu})\left(\frac{|J_1(U_{0,\mu})|}{J_1^2(U_{0,\mu})} - \frac{n_{core}^2}{n_{clad}^2}\frac{|K_1(W_{0,\mu})|}{K_1^2(W_{0,\mu})}\right)}$$ (6b)

$$P_{ratio}|_{HE}^{EH} = \frac{1}{n_{clad}k^3 a^2 n_{core}^2}\sum_{\nu,\mu}$$ (6c)

$$\frac{\beta_{\nu,\mu}\left(a_1^2|J_{\nu-1}(U_{\nu,\mu})| + a_2^2|J_{\nu+1}(U_{\nu,\mu})| + \frac{U_{\nu,\mu}^2}{2\beta_{\nu,\mu}^2 a^2}|J_\nu(U_{\nu,\mu})|\right)}{\left[\frac{a_1a_3|J_{\nu-1}| + a_2a_4|J_{\nu+1}|}{J_\nu^2(U_{\nu,\mu})} - \frac{U_{\nu,\mu}^2}{W_{\nu,\mu}^2}\frac{a_1a_5|K_{\nu-1}| + a_2a_6|K_{\nu+1}|}{K_\nu^2(W_{\nu,\mu})}\right]J_\nu^2(U_{\nu,\mu})}$$

where $$|K_l| = \begin{vmatrix} K_l(W_{\nu,\mu}) & K_{l+1}(W_{\nu,\mu}) \\ K_{l-1}(W_{\nu,\mu}) & K_l(W_{\nu,\mu}) \end{vmatrix} \text{ and } |J_l| = \begin{vmatrix} J_l(U_{\nu,\mu}) & J_{l+1}(U_{\nu,\mu}) \\ J_{l-1}(U_{\nu,\mu}) & J_l(U_{\nu,\mu}) \end{vmatrix}.$$

In Equation (6c) the original result was multiplied by two in order to account for both odd and even modes. The total power efficiency is given by the sum of the power efficiency of each mode.

Figure 4:
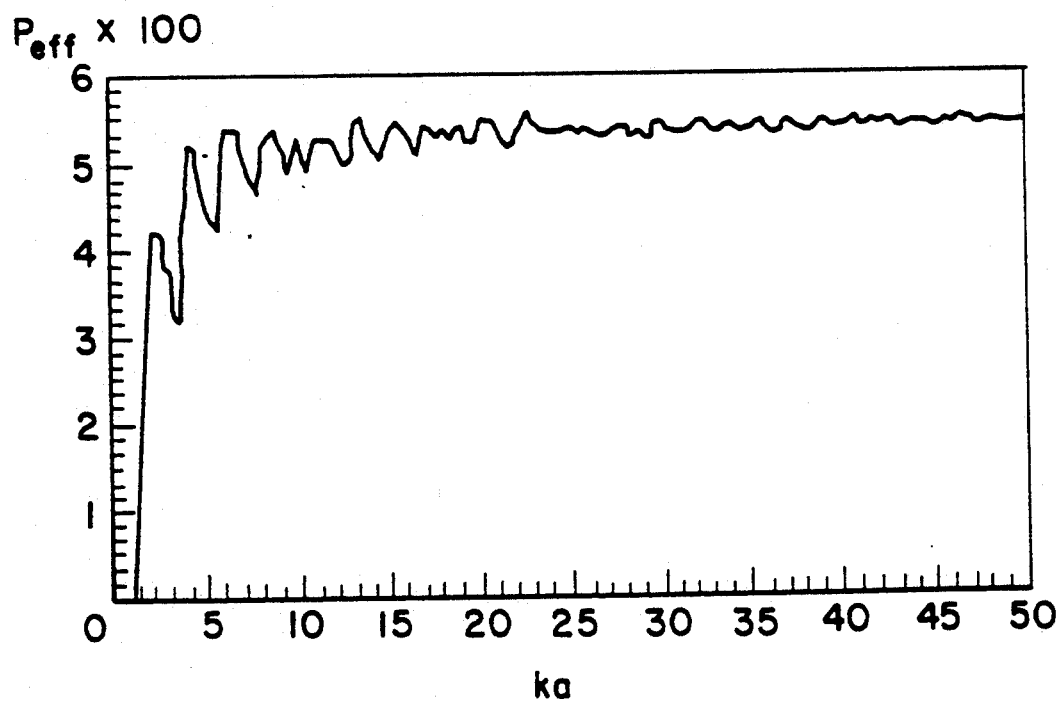
FIG. 4 is a graph of the power efficiency versus the factor ka.

It was found previously that for a distribution of sources in the cladding—as opposed to the core—the factor $ka = 2\pi a/\lambda$ is a new independent variable. See NASA Contractor Report 4333, discussed in the Background section of the present application. This result has its theoretical relevance in the sense that it decreases by one the number of independent variables making it easier to analyze the behavior of $P_{eff}$. This can be seen by substituting $\beta_{\nu,\mu} = kn_{\nu,\mu}$, where $n_{\nu,\mu}$ ($n_{clad} < n_{\nu,\mu} < n_{core}$) is the effective index of refraction, into Equations (6). By doing so the factor ka is isolated and in this way the result is also applicable to a core distribution of sources. FIG. 4 shows $P_{eff}$ plotted as a function of the factor ka wherein the indices of refraction for the core and the cladding are held fixed at $n_{core} = 1.46$ and $n_{clad} = 1.3$. Notice that $P_{eff}$ increases in the low V-number region. However, in the high V-number region, $P_{eff}$ tends to be constant, i.e. stabilizes after an increase in ka. Accordingly, a desired increase in power efficiency is obtained by increasing the factor ka. This increase may be accomplished by increasing only a, decreasing only $\lambda$, or increasing a and decreasing $\lambda$. This result is qualitatively similar to the one of a thin film cladding source fiber. However, one must point out that this similarity is only coincidental since a fiber with a thin film cladding source is a system completely different from a fiber with a core source.

The wavelength $\lambda$ of light produced by a bare active fiber core or two-stage fluorosensor is normally in the visible range of $0.4~\mu m < \lambda < 0.7~\mu m$. The core radius a of most commercially available optical fibers is in the range of $10~\mu m < a < 10^3~\mu m$. Accordingly, a typical range for the optimizing factor ka is from approximately 90 to approximately $1.6 \times 10^4$.

Figure 5:
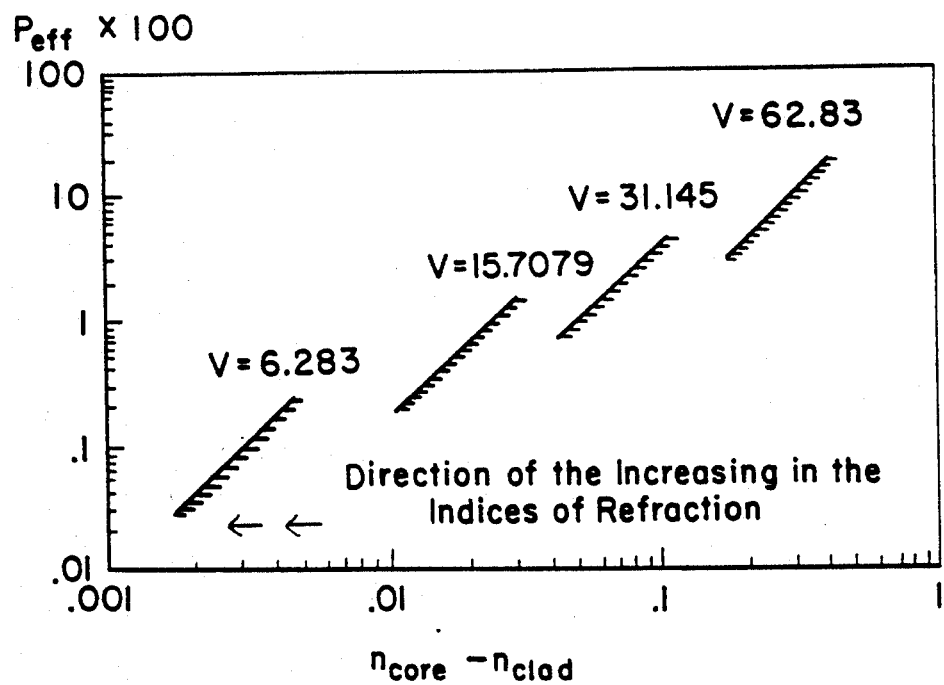
FIG. 5 is a graph of the power efficiency versus the difference in core and cladding refraction indices.

FIG. 5 illustrates how the power efficiency behaves with the difference $n_{core} - n_{clad}$ at constant V for core sources. This graph was obtained for four different V-numbers and was plotted on a log-log scale. The wavelength $\lambda$ was $0.6~\mu m$, the core radius a was $6.0~\mu m$ and the indices of refraction were defined as $3.07 < n_{core} < n_{clad} < 1.0$. Notice that these curves can easily be fitted into a linear equation. The behavior of $P_{eff}$ in FIG. 5 is essentially similar to the one exhibited by the cladding source distribution as discussed in parent U.S. patent application Ser. No. 07/761,198, filed Sept. 16, 1991, the specification of which is hereby incorporated by reference. The higher the difference between the indices of refraction, the more power is guided through the waveguide. This difference should be greater than approximately 0.1, i.e., is not the conventional weakly guiding case wherein the difference is less than 0.01. It should be noted that increasing the factor ka as described herein improves the power efficiency for both weakly and strongly guiding cases.

Figure 6:
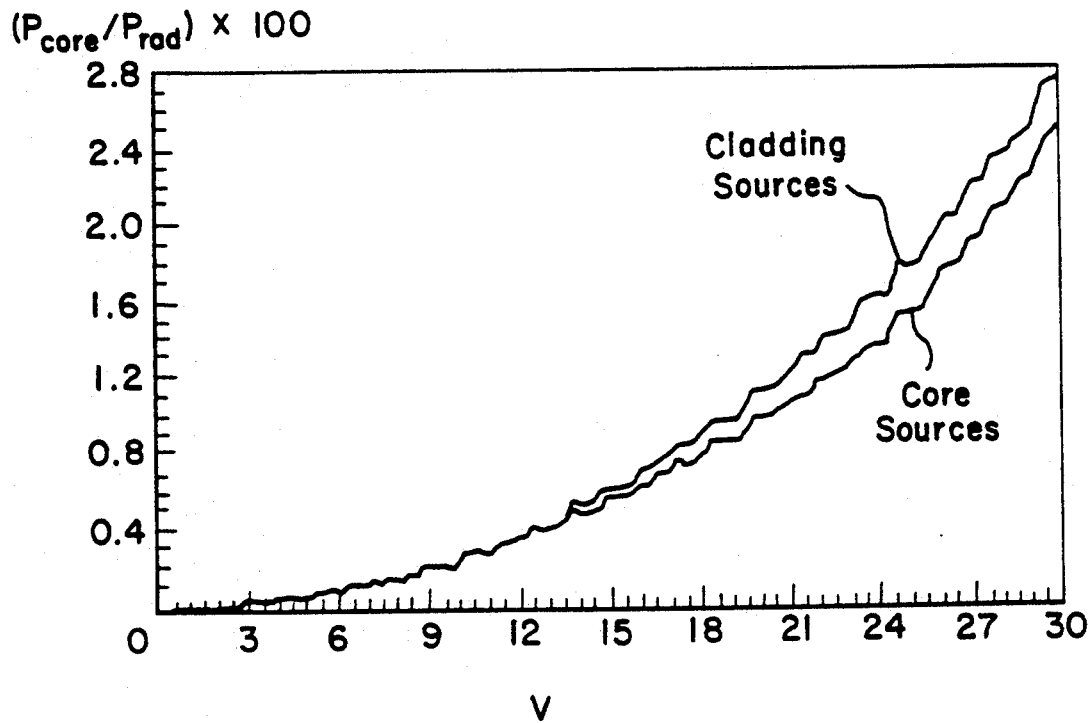
FIG. 6 is a graph of power efficiency of a thin film distribution of sources versus V-number for both core and cladding sources.

FIG. 6 graphs the power efficiency versus V-number (weakly guiding case) for a thin film source distribution just inside the core, i.e., core sources, with previous results for a thin film distribution just outside the core (clading sources) as shown in FIG. 2 of the related application, Ser. No. 07/761,198. The power efficiency was found to be slightly lesser for the first case with core sources. This difference can be explained by the fact that, at the core/cladding boundary, the normal component of the electric field just inside the interface is less than the normal component just outside the interface. Also, $P_{core}$ is a function of the intensity of the electric field inside the region of sources such that a higher field intensity results in a higher $P_{eff}$. Since the field intensity just outside the interface (thin film cladding source) is greater than the field intensity just inside the interface (thin film core sources), the higher $P_{eff}$ for thin film cladding sources is not unexpected. The core source curve of FIG. 6 was generated using a FORTRAN program employing equation (4) to compute $P_{ratio}$ for a thin film distribution of sources just inside the core/cladding interface of a fiber. The following parameters were used for both cases: $\lambda = 1.3~\mu m$, $n_{core} = 1.46$, $a = 10.0~\mu m$, $b = 50.0~\mu m$ and $n_{clad}$ was varied from 1.4599 at $V = 0.05$ to 1.322 at $V = 29.95$.

It was found that $P_{eff}$ for core sources always increases with the difference in the indices of refraction $n_{core} - n_{clad}$. This behavior is similar to the behavior exhibited by cladding sources. $P_{eff}$ was also plotted against the ka factor. It was found that there is an increase in the value of $P_{eff}$ for small V-number (small ka values). However, in the region of high V-number (high ka values), $P_{eff}$ is almost constant. These results show that a fiber than has a large core with a big difference between the core/cladding indices of refraction and is doped with a fluorescent source that emits light of low wavelength has a better efficiency.

Due to the infinite cladding approximation, the power efficiency does not involve the cladding radius, b, at all. Additional work is required to determine a more accurate behavior of $P_{eff}$ with b. Other index profiles and fiber geometries should also be worth modeling.

Many modifications, substitutions, and improvements will be apparent to the skilled artisan without departing from the spirit and scope of the present invention as defined herein and described in the following claims.

We claim:

1. A process for obtaining a desired power efficiency of an optical fiber comprising the steps of:
providing active fiber cores which produce waves of light upon excitation, the fiber cores having various respective core radii and producing light waves having various respective wavelengths; and
increasing a factor ka until the desired power efficiency is obtained, wherein a is the radius of a particular active fiber core and $k = 2\pi/\lambda$, wherein $\lambda$ is the wavelength of the light waves produced by the particular active fiber core upon excitation; and
selecting the active fiber core characterized by the factor ka which produces the desired power efficiency.

2. The process according to claim 1, wherein the factor ka is increased until the power efficiency of the optical fiber stabilizes after an initial increase.

3. The process according to claim 1, further comprising surrounding a portion of the particular active fiber core with an active cladding which produces waves of light upon excitation and wherein the particular active fiber core is provided with fluorescent substances which produce light when excited by the light produced by the excited active cladding.

4. The process according to claim 1, further comprising surrounding another portion of the particular active fiber core with an inactive guide cladding which guides the light.

5. The process according to claim 3, further comprising increasing a difference between $n_{core} - n_{clad}$, wherein $n_{core}$ is the index of refraction of the particular active fiber core and $n_{clad}$ is the index of refraction of the active cladding.

6. The process according to claim 5, wherein the difference between the respective indices of refraction of the core and cladding is greater than approximately 0.01.

7. The process according to claim 5, wherein the respective indices of refraction are related by the following: $3.0 > n_{core} > n_{clad} > 1.0$.

8. The process according to claim 1, wherein the factor ka is in the range of approximately 90 to approximately $1.6 \times 10^4$.

9. The process according to claim 1, wherein the respective radii a of the active cores are in the range of 10 $\mu$m to $10^3$ $\mu$m.

10. The process according to claim 1, wherein the active fiber cores product light having wavelengths $\lambda$ in the visible range.

11. The process according to claim 1, wherein the active fiber cores produce light having wavelengths in the range of 0.4 $\mu$m to 0.7 $\mu$m.

12. An optical fiber having a desired power efficiency prepared by a process comprising the steps of:
providing active fiber cores which produce waves of light upon excitation, the fiber cores having various respective core radii and producing light waves having various respective wavelengths;
increasing a factor ka until the desired power efficiency is obtained, wherein a is the radius of a particular active fiber core and $k = 2\pi/\lambda$, wherein $\lambda$ is the wavelength of the light waves produced by the particular active fiber core upon excitation; and
selecting the active fiber core characterized by the factor ka which produces the desired power efficiency.

13. The optical fiber according to claim 12, wherein said active fiber core contains chemiluminescent substances which react with an analyte to produce light and wherein said active core is permeable by the analyte.

14. The optical fiber according to claim 12, wherein said active fiber core contains fluoroluminescent substances which produce light upon excitation by an outside light source.

15. The optical fiber according to claim 12, wherein the factor ka is increased until the power efficiency of the optical fiber stabilizes after an initial increase.

16. The optical fiber prepared by the process according to claim 12, further comprising surrounding a portion of the particular active fiber core with an active cladding which produces waves of light upon excitation and wherein the particular active fiber core is provided with fluorescent substances which produce light when excited by light produced by the excited active cladding.

17. The optical fiber according to claim 16, wherein the active cladding is permeable to an analyte.

18. The optical fiber according to claim 16, wherein the active fiber core contains chemiluminescent substances which react with the analyte to produce light.

19. The optical fiber according to claim 16, wherein the active fiber core contains fluoroluminescent substances which are excited by an outside light source to produce light.

20. The optical fiber prepared by the process according to claim 16, further comprising increasing a difference between the index of refraction of the active cladding and the index of refraction of the particular active fiber core to further improve the power efficiency of the optical fiber.

21. The optical fiber prepared by the process according to claim 20, wherein the difference between the respective indices of refraction is greater than approximately 0.01, wherein the index of refraction of the active core is greater than the index of refraction of the active cladding.

22. The optical fiber prepared by the process according to claim 20, wherein the respective indices of refraction are related by the following: $3.0 > n_{core} > n_{clad} > 1.0$, wherein $n_{clad}$ is the index of refraction of the active cladding and $n_{core}$ is the index of refraction of the particular active fiber core.

23. The process according to claim 12, wherein the factor ka is in the range of approximately 90 to approximately $1.6 \times 10^4$.

24. The optical fiber prepared by the process according to claim 12, wherein the respective radii a of the active cores are in the range of 10 μm to $10^3$ μm.

25. The optical fiber prepared by the process according to claim 12, wherein the active fiber cores produce light having wavelengths λ in the visible range.

26. The optical fiber prepared by the process according to claim 12, wherein the active fiber cores produce light having wavelengths in the range of 0.4 μm to 0.7 μm.

* * * * *